(12) United States Patent
Cotte et al.

(10) Patent No.: US 7,807,439 B2
(45) Date of Patent: Oct. 5, 2010

(54) STAPHYLOCOCCUS AUREUS-SPECIFIC DETECTION MEDIA AND IDENTIFYING AND/OR COUNTING METHOD USING SAME

(75) Inventors: Christine Cotte, Saint-Savin (FR);
Sylvain Orenga, Neuville sur Ain (FR);
Andréa Re, Tassin la Demi-Lune (FR);
Denis Robichon, Blyes (FR)

(73) Assignee: Biomerieux S.A., Mary l'Etoile (FR)

( * ) Notice: Subject to any disclaimer, the term of this patent is extended or adjusted under 35 U.S.C. 154(b) by 1302 days.

(21) Appl. No.: 10/473,835

(22) PCT Filed: Mar. 29, 2002

(86) PCT No.: PCT/FR02/01120

§ 371 (c)(1),
(2), (4) Date: Feb. 18, 2004

(87) PCT Pub. No.: WO02/079486

PCT Pub. Date: Oct. 10, 2002

(65) Prior Publication Data

US 2004/0121404 A1    Jun. 24, 2004

(30) Foreign Application Priority Data

Mar. 30, 2001   (FR) .................................. 01 04322

(51) Int. Cl.
| | | |
|---|---|---|
| C12N 1/00 | (2006.01) | |
| C12N 1/12 | (2006.01) | |
| C12N 1/20 | (2006.01) | |
| G01N 33/569 | (2006.01) | |
| C12Q 1/20 | (2006.01) | |
| A61K 39/38 | (2006.01) | |
| A61K 39/085 | (2006.01) | |

(52) U.S. Cl. ................. 435/243; 435/252.1; 435/253.6; 435/7.33; 435/33; 424/184.1; 424/243.1

(58) Field of Classification Search .............. 424/184.1, 424/237.1; 435/4, 6, 7.1, 7.2, 7.32, 7.33
See application file for complete search history.

(56) References Cited

U.S. PATENT DOCUMENTS 5,716,799 A * 2/1998 Rambach .................. 435/34
5,962,251 A * 10/1999 Rambach .................. 435/34
6,548,268 B1 * 4/2003 Rambach .................. 435/34

FOREIGN PATENT DOCUMENTS

| WO | WO95/20674 A | 8/1995 |
| WO | WO98/55644 A | 12/1998 |
| WO | WO99/50438 A | 10/1999 |
| WO | WO 00/53799 | * 9/2000 |
| WO | WO00/53799 A | 9/2000 |

OTHER PUBLICATIONS

Isik et al (International Journal of Systematic Bacteriology, 1999, 49, 1227-1230).*
van Netten et al (Int. J Food Microbiol., Jul. 1999, 8(4):299-316)(Abstract only).*
von Graevenitz et al (APMIS, May 1994; 102(5):381-9) (Abstract only).*
Chadwick et al (Clin. Microbiol. Infect., 1997; 3(5):559-563)(Abstract only).*
Fontana et al (European J. Clin. Microbiol. Infect. Dis., vol. 16, 1997).*
Raus et al (Journal of Clinical Microbiology, Oct. 1983, p. 789-792).*
S. Bascomb et al., "Use of Enzyme tests in characterization and identification of aerobic and facultatively anaerobic Gram-positive cocci", *Clinical Microbiology Review*, 11(2): 318-340 (Apr. 1998).
J.A. Lindsay et al., "Identification of *Staphylococcus epidermidis* and *Staphylococcus hominis* from blood cultures by testing susceptibility to desferrioxamine", *European Journal of Clinical Microbiology & Infection Diseases* 12:127-131 (1993).

* cited by examiner

*Primary Examiner*—Vanessa L. Ford
(74) *Attorney, Agent, or Firm*—Drinker Biddle & Reath LLP

(57) ABSTRACT

The invention concerns a medium for specific detection of *Staphylococcus aureus* and/or discrimination between positive-coagulase *Staphylococcus* and negative-coagulase enabling *Staphylococcus* to isolate bacteria of the genus staphylococcus and identify the *Staphylococcus aureus* species, which use at least an enzymatic substrate, preferably a chromogenic or fluorescent agent, and still more preferably consisting of an indoxyl or naphthol base. The invention also concerns a method for identifying, and optionally counting, *Staphylococcus aureus* using such a medium. It consists of a *Staphylococcus aureus* culture medium and at least an enzymatic substrate enabling testing of an α-glucosidase activity. The invention is particularly applicable in the field of diagnosis.

14 Claims, No Drawings

STAPHYLOCOCCUS AUREUS-SPECIFIC DETECTION MEDIA AND IDENTIFYING AND/OR COUNTING METHOD USING SAME

The present invention relates to a medium for the specific detection of *Staphylococcus aureus* and/or for the discrimination of coagulase-positive *Staphylococcus* compared to coagulase-negative *Staphylococcus*, making it possible to isolate bacteria of the *staphylococcus* genus and to identify the species *Staphylococcus aureus*, which use at least one enzyme substrate. It also relates to a method for identifying, and optionally counting, *Staphylococcus aureus*, which uses such a medium.

In 1999, the *Staphylococcus* genus included forty-three (43) species and subspecies, seventeen (17) of which were found in humans. Most of these species are opportunistic pathogens in humans exhibiting a high risk in the event of a skin injury due to a trauma or to direct implantation of a medical product. Moreover, the species *Staphylococcus aureus* is a bacterium which is often found in patients who must receive hospital treatment involving devices such as syringes or catheters. There is therefore a great value in detecting the presence of this pathogenic bacterium, which is increasingly involved in nosocomial diseases.

Among the staphylococci, *Staphylococcus aureus* is unquestionably the most virulent species since it produces a large number of extracellular enzymes and toxins. It can be the cause of many and varied pathological conditions, ranging from simple whitlow to the most serious infections such as septicaemia, endocarditis, pneumopathy or osteoarticular infections, for which the prognosis can be not very optimistic.

In addition, only five (5) species: *Staphylococcus aureus*, *Staphylococcus epidermidis*, *Staphylococcus haemolyticus*, *Staphylococcus saprophyticus* and *Staphylococcus hominis* represent at least 1% of the pathogenic strains isolated in clinical centres and they alone represent more than 98% of the staphylococcal strains most commonly encountered. The other species are rarely encountered and are relatively non-pathogenic.

In bacteriology, it is conventional to contrast these species *Staphylococcus aureus*, characterized by the production of a coagulase, with the other "coagulase-negative" species.

Conventional methods for differentiating *Staphylococcus aureus* from *Staphylococcus* not of the *aureus* genus are based on searching for free coagulase and for DNase and on obtaining agglutination on latex aimed at demonstrating the presence of fibrinogen affinity factor, of protein A and of capsular antigens.

It should be noted that other potentially pathogenic staphylococcal species are capable of expressing a coagulase.

The coagulase-positive species are as follows: *Staphylococcus aureus*, *Staphylococcus intermedius*, *Staphylococcus hyicus*, *Staphylococcus delphinis*, *Staphylococcus lutrae* and *Staphylococcus schleiferi*.

Techniques for culturing on selective media exist for evaluating the presence of *Staphylococcus aureus*. They are the following media:

Chapman high salt medium (containing 75% of NaCl) is generally selective for *Staphylococcus aureus* and staphylococci which hydrolyse mannitol. These bacteria turn the medium from red to yellow. Some microorganisms and the group D enterococci, in particular, can produce the same reaction on the medium; it is therefore necessary to verify the catalase (negative for streptococci).

Baird Parker medium (containing potassium tellurite and lithium chloride as selective agents) is used to isolate and count coagulase-positive staphylococci in food products and makes it possible to demonstrate the activity of the coagulase. On this medium, the colonies of *Staphylococcus aureus*, and of other coagulase-positive species, appear with a black centre surrounded by an opaque ring. Other microorganisms can develop on this medium. This involves mainly the following groups:

Gram + Cocci: of the *Enterococcus* and *Listeria* genera,
Gram − Bacille: of the *Proteus et Pseudomonas* genera.

In fact, the detection of *Staphylococcus aureus* which uses the Chapman high salt medium technique lacks sensitivity (capacity to demonstrate the species sought when said species is present in low amount in a biological sample to be tested) and especially specificity (capacity to detect the species sought in the biological sample to be tested containing other species).

Similarly, the detection of *Staphylococcus aureus* which uses the Baird-Parker medium technique lacks sensitivity and specificity. Thus, certain strains which do not belong to the species *Staphylococcus aureus*, in particular *Staphylococcus schleiferi* and *Staphylococcus saprophyticus*, can also give colonies surrounded by a lightening halo. It may also be that some strains of *Staphylococcus aureus* do not express the enzyme activity sought or do not develop in the medium, because they may be present in too small an amount in the biological samples and/or they may be inhibited by components in the medium which are too selective.

It is therefore understood that this detection with the Baird-Parker and Chapman media gives only a presumptive diagnosis and requires other tests for confirmation. Now, the additional handling required to identify *Staphylococcus aureus* increases the duration and the cost of the analyses. It requires a multitude of reagents and the involvement of qualified personnel.

It is also possible to use glucosidase-based substrates which make it possible to detect, depending on the configuration of the molecules used, either α-glucosidase activity or β-glucosidase activity.

The use of α-glucosides for identifying the various staphylococcal species is already known. However, studying the acidification of these sugars by the various staphylococcal species does not currently allow simple identification of *Staphylococcus aureus*, since it is either not specific enough (in the case of maltose, turanose, sucrose, trehalose for example) or not sensitive enough (in the case of methyl-α-glucoside, raffinose, turanose for example) (Bascomb S. and Manafi M. 1998. Use of enzyme tests in characterization and identification of aerobic and facultatively anaerobic Gram positive cocci. Clin. Microbiolol. Rev. 11: 318-340.) (Kloos W E. et al. 1982. Identification of *Staphylococcus Species* with the API Staph -IDENT. System. J. Clin. Microbiol. 16 (3): 509-516.). This state of affairs does not tend to encourage research scientists to work on this type of α-glucosidase activity.

On the other hand, recent publications refer to the advantage of working with β-glucosidase activity. This is, for example, the case of patent EP-B-0.741.797, which describes a method for differentiating, on a selective culture medium, bacteria of the *Staphylococcus* genus from other bacteria, using two indoxyl-based chromogenic substrates making it possible to detect the phosphatase activity of the staphylococci and the β-glucosidase activity of the other bacterial genera.

Compared to the detection of staphylococci on a gel medium, according to that patent, making it possible only to differentiate staphylococci from bacteria of other genera, our invention therefore makes it possible to distinguish *Staphylococcus aureus* from the other bacteria of the *Staphylococcus* genus.

In an article "Evaluation of CHROMagar Staph. aureus, a new chromogenic medium, for isolation and presumptive identification of *Staphylococcus aureus* from human clinical specimens." by Gaillot O. et al., 2000, J. Clin. Microbiol. 38, 4, 1587-1591, a chromogenic culture medium, CHROMagar (trademark) Staph. Aureus (catalogue number TA600, CHROMagar, Paris, France), for isolating staphylococci and identifying *Staphylococcus aureus* using chromogenic substrates which provide a purple coloration of the latter species, is described and evaluated. The other species of the same genus are then detected in that they are coloured blue or are colourless, in theory. Use is essentially made of β-glucosidase, β-glucuronidase, β-galactosidase and phosphatase activities, and also an inhibitor, Deferoxamine, which makes it possible to differentiate *Staphylococcus aureus* and *Staphylococcus epidermidis*. A patent application has, moreover, been filed on this subject, WO-A-00/53799. That patent application proposes a medium for detecting *Staphylococcus aureus* which couples at least the following two chromogenic agents:

5-bromo-6-chloro-3-indoxyl phosphate, phosphatase activity, and 5-bromo-4-chloro-3-indoxyl glucoside, β-glucosidase activity, already described in patent application EP-B-0.741.797, described above. In fact, this new document simply and essentially adds a growth inhibitor, called Deferoxamine, to the chromogens. The said Deferoxamine makes it possible to discriminate more clearly *Staphylococcus aureus* from *Staphylococcus epidermidis*. Now, Deferoxamine is already well known as a growth inhibitor for *Staphylococcus epidermidis* but not for the other staphylococcal species (Lindsay J. A., Aravena-roman M. A., Riley T. V.—Identification of *Staphylococcus epidermidis* and *Staphylococcus hominis* from blood cultures by testing susceptibility to desferrioxamine—European J. of Clin. Microbiol. et Inf. Diseases —1993, vol. 12, pages 127-131).

Compared to the CHROMagar (trademark) Staph. aureus medium, our medium makes it possible to differentiate *Staphylococcus aureus* from *Staphylococcus epidermidis* more easily, the two species producing colonies of the same colour on the CHROMagar (trademark) medium. This is due to the lack of specificity of the phosphatase substrates, which are positive for *Staphylococcus aureus* and *Staphylococcus epidermidis*, and to the fact that the inhibition of the latter by the Deferoxamine is only partial.

It should be noted that, according to our invention, by detecting only the α-glucosidase activity, it is already possible to separate *Staphylococcus aureus* from *Staphylococcus epidermidis* and *Staphylococcus saprophyticus*, which are three of the main staphylococcal species isolated clinically.

In fact, and against all expectations, the inventors have demonstrated that α-glucoside-based substrates can allow sensitive and specific identification of *Staphylococcus aureus*. Specifically, through the choice of operating conditions and/or of particular α-glucosidase substrates and/or of coupling at least a second enzyme substrate making it possible to define a reaction medium, it is possible:

to discriminate between the main coagulase-positive staphylococcal species most commonly isolated (*Staphylococcus aureus* and *Staphylococcus intermedius* essentially) and the coagulase-negative staphylococci most commonly present (*Staphylococcus epidermidis, Staphylococcus haemolyticus, Staphylococcus saprophyticus* essentially), and/or to specifically identify *Staphylococcus aureus*.

For example, a gain in specificity and in the practical aspect of the invention is provided by adding at least a second enzyme substrate. Thus, this gain is obtained by the detection, firstly, of α-glucosidase activity, which activity is strongly expressed by *Staphylococcus aureus* and very weakly by the other staphylococcal species and, secondly, of β-glucuronidase and/or β3-galactosidase and/or β-glucosidase activity expressed by most staphylococci but not by *Staphylococcus aureus*, as a function of the substrates used. This second activity makes it possible to more clearly differentiate *Staphylococcus aureus* from the other species of the *Staphylococcus* genus.

To this effect, the present invention relates to a medium for the detection of *Staphylococcus aureus* and/or of coagulase-positive Staphylococci, which comprises a *Staphylococcus aureus* culture medium and at least one enzyme substrate for demonstrating α-glucosidase activity.

The enzyme substrate for demonstrating α-glucosidase activity is a chromogenic or fluorescent agent.

According to a first variant of implementation, the chromogenic or fluorescent agent for demonstrating α-glucosidase activity is indoxyl-based or umbelliferone-based, so as to allow the detection of *Staphylococcus aureus* and of the coagulase-positive Staphylococci.

According to the first variant of implementation, this medium uses as chromogenic agent(s):

6-bromo-3-indoxyl-α-D-glucoside, 5-bromo-4-chloro-3-indoxyl-α-D-glucoside, 5-bromo-4-chloro-3-indoxyl-N-methyl-α-D-glucoside, 6-chloro-3-indoxyl-α-D-glucoside, and/or 4-methylumbelliferyl-α-D-glucoside.

According to a second variant of implementation, the chromogenic agent for demonstrating α-glucosidase activity is naphthol-based, so as to allow the detection of *Staphylococcus aureus*.

According to the second variant of implementation, this medium uses as chromogenic agent: 2-naphthyl-α-D-glucopyranoside.

According to one embodiment, the medium uses at least two different enzyme substrates, preferably two chromogenic agents, one for demonstrating α-glucosidase activity and the other for detecting osidase (β-glucosidase and/or β-glucuronidase and/or β-galactosidase) and/or esterase (esterase/lipase and/or phosphatase and/or sulphatase) and/or peptidase and/or coagulase activity.

In addition, the medium uses two chromogenic agents chosen from the following pairs:

5-bromo-4-chloro-3-indoxyl-N-methyl-α-D-glucoside combined with 5-bromo-6-chloro-3-indoxyl-β-D-galactoside, or 5-bromo-4-chloro-3-indoxyl-N-methyl-α-D-glucoside combined with 6-chloro-3-indoxyl-β-D-glucuronide, or 6-chloro-3-indoxyl-α-D-glucoside combined with 5-bromo-4-chloro-3-indoxyl-β-D-glucuronide, or 6-chloro-3-indoxyl-α-D-glucoside combined with 5-bromo-4-chloro-3-indoxyl-β-D-glucoside.

Preferably, the medium uses at least one inhibitor which favours growth of bacteria of the *Staphylococcus* genus, such as lithium chloride (LiCl), sodium azide (NaN3), colistin, amphotericin, aztreonam, colimicin, sodium chloride (NaCl) or Deferoxamine.

According to one variant of the implementation, the medium uses a mixture of inhibitors, comprising four inhibitors, which favours the growth of bacteria of the *Staphylococcus* genus, which inhibitors are:

LiCl,
O/129,
aztreonam, and
amphotericin.

According to another variant, the medium uses maltose, preferably at a concentration of between 100 and 300 mg/l.

The present invention also relates to a method for identifying one or more bacteria of the species *Staphylococcus aureus* in a sample, containing at least one species of bacterium, which comprises the following steps:

- inoculating a medium, as described above, with all or part of the sample, and
- incubating the inoculated medium so as to produce bacterial colonies of sufficient size to observe the coloration of each chromogenic agent or the fluorescence of each fluorescent agent, which has reacted, using said medium.

This method may also make it possible to count one or more bacteria of the species *Staphylococcus aureus* in the sample; in this case, a third step is carried out, which consists in counting the colonies identified by a coloration or a fluorescence related to bacteria of the species *Staphylococcus aureus*.

Experiment 1: Evaluation of Various α-glucosidase Substrates Consisting of Various Indoxyl Derivative-Based Chromogenic Markers:

The media below were prepared in a base containing:
11 grams per liter (g/l) of peptone,
0.65 g/l of TRIS buffer, and
14 g/l of agar, in combination with the chromogenic α-glucosidase substrates described in table 1 below:

TABLE 1

| Abbreviations for the chromogenic α-glucosidase substrates used | |
|---|---|
| Chromogenic substrate | Abbreviation used |
| 5-bromo-4-chloro-3-indoxyl-α-D-glucoside | 5-bromo-4-chloro-3-indoxyl-α-D-glucoside |
| 6-Chloro-3-indoxyl-α-D-glucoside | Pink-a-GLU |
| 6-Bromo-3-indoxyl-α-D-glucoside | Red "A" a-GLU |

TABLE 1-continued

| Abbreviations for the chromogenic α-glucosidase substrates used | |
|---|---|
| Chromogenic substrate | Abbreviation used |
| 5-Bromo-4-chloro-3-indoxyl-N-methyl-α-D-glucoside | Green "A" a-GLU |

The α-glucosidase substrates are solubilized in dimethyl sulfoxide at a concentration of 200 g/l. A sufficient volume to obtain a final concentration of substrate of 100 mg/l is added to the four molten media. Microorganisms derived from the bioMérieux internal collection were seeded onto each one of the media, on their own as three dials, using a suspension at 0.5 MacFarland. However, results obtained with microorganisms derived from collections available to the public, ATCC or NCTC for example, would give identical results. The dishes were incubated at 37° C. for 48 hours. The colonies were examined visually after an incubation time of 24 and 48 hours. The coloration and also the intensity of this coloration were noted.

In table 2 below, as in the tables which will follow, C represents the coloration of the colonies after incubation, I represents the intensity of this coloration, the symbol "–" is synonymous with a lack of colour or intensity, and, finally, TI defines the incubation time. It should be noted that the intensity of the coloration is an arbitrary scale, but which is common to all the biological samples and all the media tested. This scale is valid for this experiment and also for all the experiments which will follow. It can be defined in the following way:

0 corresponds to a lack of activity,
0.1 corresponds to the presence of a trace of coloration,
0.5 corresponds to the presence of a very pale coloration,
1 corresponds to the presence of a clear coloration of weak intensity,
1.5 corresponds to the presence of a coloration which is intermediate between colorations 1 and 2,
2 corresponds to the presence of a true coloration of medium intensity,
2.5 corresponds to the presence of a coloration which is intermediate between colorations 2 and 3,
3 corresponds to the presence of an intense coloration
3.5 corresponds to the presence of a coloration which is intermediate between colorations 3 and 4,
4 corresponds to the presence of a very intense coloration.

The results are given in table 2 below:

TABLE 2

Evaluation of various α-glucosidase substrates consisting of various indoxyl derivative-based chromogenic markers

| Strains | Media TI | X-a-GLU | | Pink-a-GLU | | Red "A" a-GLU | | Green "A" a-GLU | |
|---|---|---|---|---|---|---|---|---|---|
| | | C | I | C | I | C | I | C | I |
| S. aureus 070 | 24 h | turquoise | 1.5 | pink | 2 | pink | 2 | green | 1.5 |
| | 48 h | turquoise | 1.5 | pink | 2 | pink | 2.5 | green | 2.5 |
| S. aureus 276 | 24 h | turquoise | 2 | pink | 1.5 | pink | 2 | green | 2 |
| | 48 h | turquoise | 2 | pink | 1.5 | pink | 2 | green | 2 |
| S. aureus 004 | 24 h | turquoise | 1 | pink | 1 | pink | 0.5 | green | 1.5 |
| | 48 h | turquoise | 2 | pink | 1 | pink | 2.5 | green | 2 |
| S. intermedius 075 | 24 h | turquoise | 0.5 | — | 0 | — | 0 | green | 1.5 |
| | 48 h | turquoise | 2 | pink | 0.5 | pink | 1.5 | green | 1.5 |

TABLE 2-continued

Evaluation of various α-glucosidase substrates consisting of various indoxyl derivative-based chromogenic markers

| Strains | Media TI | X-a-GLU C | I | Pink-a-GLU C | I | Red "A" a-GLU C | I | Green "A" a-GLU C | I |
|---|---|---|---|---|---|---|---|---|---|
| S. saprophyticus 064 | 24 h | — | | 0 — | | 0 — | | 0 — | 0 |
| | 48 h | turquoise | | 0.5 — | | 0 — | | 0 — | 0 |
| S. epidermidis 009 | 24 h | — | | 0 — | | 0 — | | 0 — | 0 |
| | 48 h | turquoise | | 1 — | | 0 — | | 0 — | 0 |
| S. xylosus 008 | 24 h | turquoise | | 0.5 — | | 0 — | | 0 — | 0 |
| | 48 h | turquoise | | 1.5 pink | | 0.5 pink | | 2.5 green | 1 |

For the substrate 5-bromo-4-chloro-3-indoxyl-α-D-glucoside, a difference in intensity of coloration is obtained between the staphylococcal strains at 24 hours, which makes it possible to identify *Staphylococcus aureus* and to distinguish it from the other species of the *Staphylococcus* genus. At 48 hours, a doubt can exist between *Staphylococcus aureus* and *Staphylococcus xylosus*.

For the other three substrates, the incubation time has no influence, in the sense that the difference in intensity of coloration, at 24 hours as at 48 hours, makes it possible to identify *Staphylococcus aureus* and to distinguish it with respect to the other species of the *Staphylococcus* genus.

It is noted, however, that the differences in intensity between the *Staphylococcus aureus* strains and the *Staphylococcus xylosus* strains (coagulase-negative) are more significant with the three substrates 6-chloro-3-indoxyl-α-D-glucoside, 6-bromo-3-indoxyl-α-D-glucoside and 5-bromo-4-chloro-3-indoxyl-N-methyl-α-D-glucoside, which give a better contrast between the colour of the marker and that of the medium and are more specific than 5-bromo-4-chloro-3-indoxyl-α-D-glucoside.

Experiment 2: Differentiation of *Staphylococcus aureus* with Respect to the Species of the Same Genus by Direct Detection of the α-glucosidase Activity and of Another Osidase Activity in a Gelled Medium:

The media below were prepared in a base containing:
 11 grams per liter (g/l) of peptone,
 0.65 g/l of TRIS buffer, and
 14 g/l of agar, combined with a combination of two chromogenic substrates, one of which makes it possible to detect α-glucosidase activity. These complex substrates are given in table 3 below:

TABLE 3

Abbreviation of various combinations of chromogenic α-glucosidase substrates and of chromogenic substrates specifically for other enzyme activities

| Abbreviation | α-glucosidase substrate | Substrate combined (activity detected) |
|---|---|---|
| A | 5-bromo-4-chloro-3-indoxyl-N-methyl-α-D-glucoside | 6-chloro-3-indoxyl-β-D-glucuronide (β-glucuronidase) |
| B | 5-bromo-4-chloro-3-indoxyl-N-methyl-α-D-glucoside | 6-chloro-3-indoxyl-β-D-galactoside (β-galactosidase) |
| C | 6-chloro-3-indoxyl-α-D-glucoside | 5-bromo-4-chloro-3-indoxyl-β-D-glucoside (β-glucosidase) |
| D | 6-chloro-3-indoxyl-α-D-glucoside | 5-bromo-4-chloro-3-indoxyl-β-D-glucuronide (β-glucuronidase) |

A stock solution of each α-glucosidase at 200 g/l is prepared in dimethyl sulfoxide. A sufficient volume to obtain a final concentration for each α-glucosidase substrate of 100 mg/l is added to the four molten media. At the same time, a sufficient volume of substrate for each one of the other osidase activities, described above, is added to the four media at a concentration of between 50 and 200 mg/l depending on the substrate. Microorganisms derived from the bioMérieux internal collection were seeded onto each one of the media, on their own as three dials, using a suspension at 0.5 MacFarland. The dishes were incubated at 37° C. for 48 hours. The colonies formed were examined visually after 24 and 48 hours of incubation. The coloration and also the intensity of this coloration were noted.

The results are given in table 4 below:

TABLE 4

Evaluation of various combinations of substrates

| Strains | Media TI | A C | I | B C | I | C C | I | D C | I |
|---|---|---|---|---|---|---|---|---|---|
| S. aureus 070 | 24 h | green | 1.5 | green | 1.5 | pink | 1.5 | pink | 2 |
| | 48 h | green | 1.5 | green | 1.5 | pink | 3 | pink | 3 |
| S. aureus 276 | 24 h | green | 2 | green | 2 | pink | 1.5 | pink | 1.5 |
| | 48 h | green | 3 | green | 3 | pink | 3.5 | pink | 2 |
| S. aureus 004 | 24 h | green | 1.5 | green | 1.5 | pink | 1.5 | pink | 1.5 |
| | 48 h | green | 1.5 | green | 1.5 | pink | 2 | pink | 2 |

TABLE 4-continued

Evaluation of various combinations of substrates

| Strains | Media TI | A | | B | | C | | D | |
|---|---|---|---|---|---|---|---|---|---|
| | | C | I | C | I | C | I | C | I |
| S. intermedius 075 | 24 h | green | — | 0.5 | grey | 0.5 | pink | 0.5 | pink | 0 |
| | 48 h | green | — | 1.5 | purple | 2 | pink | 1.5 | pink | 1.5 |
| S. haemolyticus 131 | 24 h | — | — | 0 | — | 0 | pink | 0.5 | pink | 0.5 |
| | 48 h | — | — | 0 | — | 0 | pink | 0.5 | pink | 0.5 |
| S. saprophyticus 064 | 24 h | — | — | 0 | pink | 2 | — | 0 | — | 0 |
| | 48 h | — | — | 0 | pink | 2.5 | pink | 0.5 | pink | 0.5 |
| S. epidermidis 009 | 24 h | — | — | 0 | — | 0 | — | 0 | — | 0 |
| | 48 h | — | — | 0 | — | 0 | pink | 0.5 | pink | 0.5 |
| S. xylosus 008 | 24 h | pink | — | 1.5 | purple | 0.5 | turquoise | 3 | turquoise | 1.5 |
| | 48 h | purple | — | 3.5 | purple | 1.5 | turquoise | 3 | turquoise | 2.5 |

The results above show that it is possible to distinguish *Staphylococcus aureus* from the other species most commonly encountered (*Staphylococcus epidermidis*, *Staphylococcus saprophyticus*, etc.) after incubation for 24 hours with all the pairs of chromogenic substrates tested.

Each pair of substrates A, B, C and D studied using the range of colours and/or using the colour intensity makes it possible to distinguish the various staphylococcal species. Firstly, the difference in coloration makes it possible to detect *Staphylococcus xylosus* unambiguously and, secondly, the highest levels of colour intensity, obtained for *Staphylococcus aureus*, make it possible to differentiate it from the other species of the same genus having the same coloration.

Only the species *Staphylococcus intermedius* can pose a problem at 48 hours with the substrate pair A; however, there is no ambiguity at 24 hours of incubation, which is more advantageous since the shorter the identification period, the more effective the medium. This is a coagulase-positive staphylococcal species which is not distinguished from *Staphylococcus aureus* by most of the methods of identification, in particular on the Chapman, Baird Parker and CHROMagar (trademark) Staph aureus media.

Experiment 3: Comparative Study of One of our Media Containing a Mixture of Substrates Described in Experiment 2, with Respect to Commercially Available Media:

The following culture media, which detect the presence of *Staphylococcus aureus* in a biological sample, can be obtained from the following companies:

CHROMagar (trademark) Staph aureus medium (reference TA600) from the company CHROMagar in Paris, France, and Chapman (reference 43311) and Baird Parker (reference 43521) media from the company bioMérieux at Marcy l'Etoile, France.

The abbreviations for the media given in table 5 below are as follows:

A corresponds to the medium containing the mixture A described in experiment 2,

B corresponds to the CHROMagar (trademark) Staph aureus medium used to isolate staphylococci and to identify the species *Staphylococcus aureus* through pink coloration of the colonies, the other staphylococcal species give a turquoise colour or are colourless, C corresponds to the Chapman medium used to isolate *Staphylococcus aureus* and staphylococci which hydrolyse mannitol, these bacteria change the colour indicator present in the medium from red to yellow, and D corresponds to the Baird Parker medium used to isolate and characterize *Staphylococcus aureus*, which produces, in 24 hours, characteristic colonies with a black centre surrounded by a lightened zone, termed halo, corresponding to the detection of a coagulase.

Thirty-six (36) strains belonging to twelve (12) staphylococcal species, the most commonly encountered in clinical tests, were tested in the media described above. These microorganisms derived from the bioMérieux internal collection were seeded onto each one of the media, on their own as three dials, using a suspension at 0.5 McFarland. The dishes were incubated at 37° for 48 hours. The colonies formed were examined visually after 24 and 48 hours of incubation. The coloration of the colonies on our medium and on the CHROMagar (trademark) Staph aureus chromogenic medium was noted according to the method and the scale described in example 1. For reading the Chapman medium, the symbol "−" corresponds to a lack of change in the coloured indicator, the agar remains red around the colonies (mannitol−strains) and the symbol "+" corresponds to a change in the coloured indicator, the agar becomes yellow around the colonies (mannitol +strain). For reading the Baird Parker medium, the symbol "−" corresponds to a lack of lightened halo around the colonies (coagulase−strain) and the symbol "+" corresponds to the presence of a lightened halo around said colonies (coagulase+strain).

In table 5 below, the coloration corresponds to the coloration of the colonies after incubation, the initials "C. M." represent the coloration of the Chapman medium around the colonies after incubation, the "Halo" represents the lightened zone of the Baird Parker medium around the colonies after incubation, and, finally, the symbol "No" represents the number of strains per species identified, according to the medium, by the specific coloration or the halo.

TABLE 5

Comparison of a medium according to the invention with the commercially available media.

| Strains | Medium TI | A Coloration | No | B Coloration | No | C C. M. | No | D Halo | No |
|---|---|---|---|---|---|---|---|---|---|
| S. aureus | 24 h | green | 9 | pink | 9 | + | 9 | + | 3 |
| (9) | 48 h | green | 9 | pink | 9 | + | 9 | + | 5 |
| S. | 24 h | green | 2 | pink | 2 | − | — | + | 2 |
| intermedius | 48 h | green | 2 | pink | 2 | − | — | + | 2 |
| (2) | | | | | | | | | |
| S. | 24 h | — | — | — | — | + | 2 | − | — |
| haemolyticus | 48 h | — | — | — | — | + | 2 | − | — |
| (3) | | | | | | | | | |
| S. | 24 h | — | — | turquoise | 3 | + | 1 | − | — |
| saprophyticus | 48 h | — | — | turquoise | 3 | + | 1 | − | — |
| (3) | | | | | | | | | |
| S. epidermidis (5) | 24 h | — | — | pink | 4 | − | — | − | — |
|  | 48 h | — | — | pink | 4 | − | — | − | — |
| S. hominis | 24 h | — | — | turquoise | 1 | − | — | − | — |
| (2) | 48 h | — | — | turquoise | 1 | − | — | − | — |
| S. warneri | 24 h | — | — | — | — | + | 1 | − | — |
| (2) | 48 h | — | — | — | — | + | 1 | − | — |
| S. schleiferi | 24 h | — | — | pink | 2 | − | — | + | 2 |
| (2) | 48 h | — | — | pink | 2 | − | — | + | 2 |
| S. cohnii | 24 h | pink | 1 | turquoise | 1 | + | 2 | − | — |
| (2) | 48 h | pink | 1 | turquoise | 2 | + | 2 | − | — |
| S. xylosus | 24 h | pink | 2 | turquoise | 2 | + | 1 | − | — |
| (2) | 48 h | purple | 2 | turquoise | 2 | + | 2 | − | — |
| S. capitis | 24 h | — | — | — | — | + | 1 | − | — |
| (2) | 48 h | — | — | — | — | + | 2 | − | — |
| S. hyicus | 24 h | — | — | pink | 2 | − | — | − | — |
| (2) | 48 h | — | — | purple | 2 | − | — | + | 2 |

All the strains of Staphylococcus aureus were identified on the medium according to the invention and on the CHROMagar (trademark) Staph aureus and Chapman media. In addition, the strains of Staphylococcus intermedius, a coagulase-positive species, are identified on our medium, according to the invention, as on the CHROMagar (trademark) Staph aureus and Baird Parker media. The results also show that no false positive was identified on the medium according to the invention and on the Baird Parker medium. It is also noted that, on the CHROMagar (trademark) Staph aureus medium and on the Chapman high salt medium. (containing 75% NaCl), it is not possible to distinguish Staphylococcus aureus from certain coagulase-negative species. It is therefore necessary to carry out additional tests aimed at demonstrating the presence of this Staphylococcus aureus.

This experiment demonstrates the specificity and the reliability of the method according to the invention.

Experiment 4: Evaluation of Various Operating Conditions with a Medium Containing a Naphthol Derivative-Based α-glucosidase Substrate:

The experiment below was carried out in a liquid medium and in the presence of naphthol derivative-based chromogenic substrates.

The medium and the substrates are distributed into API "galleries" (trademark) produced by the company bioMérieux at Marcy l'Etoile, France.

These "galleries" constitute a semi-quantitative method for searching for enzyme activities in microorganisms and make it possible to rapidly and simultaneously study nineteen enzyme activities. Each "gallery" comprises twenty cupules in which the solutions containing the enzyme substrates are distributed. The enzyme assays are carried out by distributing 65 μl of bacterial suspension at 5-6 McFarland into each cupule.

The intensity of coloration for each cupule is examined visually after 4 hours of incubation at 37° C. and after the addition of appropriate reagents: ZYM A (ref.: 70470) and ZYM B (ref.: 70480), which can be obtained from bioMérieux also mentioned above. The intensity of coloration will be directly proportional to the amount of substrate hydrolysed by the enzyme.

The values for the intensity of coloration are then marked on a results sheet according to the following classification: the mark 0 corresponds to a negative reaction, the mark 5 to a reaction of maximum intensity, marks 1, 2, 3 and 4 indicate intermediate levels of coloration and therefore of enzyme activity. More detailed information on this marking can be found in the API reading scale provided with the "galleries" of the same name.

As in experiments 1 or 2, the microorganisms are derived from the bioMérieux internal collection.

The enzyme activity sought and the corresponding naphthol derivative substrates are described in table 6 below:

TABLE 6

List of the enzyme activities sought using the chromogenic substrates consisting of naphthol derivatives.

| No | ENZYME SOUGHT | SUBSTRATE |
|---|---|---|
| 1 | Control | none |
| 2 | Phosphatase alkaline | 2-naphthyl-phosphate |
| 3 | α-galactosidase | 6-bromo-2-naphthyl-α-D-galactopyranoside |
| 4 | β-galactosidase | 2-naphthyl-β-D-galactopyranoside |
| 5 | β-glucuronidase | naphthol-β-D-glucuronide |
| 6 | α-glucosidase | 2-naphthyl-α-D-glucopyranoside |
| 7 | β-glucosidase | 6-bromo-2-naphtyl-β-D-glucopyranoside |

The results of the enzyme activities are given in table 7 below:

TABLE 7

Identification of the strains of *Staphylococcus aureus*
positive by detection of α-glucosidase activity
compared to other staphylococcal species.

| No | S. aureus 276 | S. saprophyticus 009 | S. epidermidis 103 | S. haemolyticus 137 | S. intermedius 075 |
|---|---|---|---|---|---|
| 1 | Colourless | Colourless | Colourless | Colourless | Colourless |
| 2 | 2 | 1 | 3 | 0 | 4 |
| 3 | 0 | 0 | 0 | 0 | 0 |
| 4 | 0 | 3 | 0 | 0 | 3 |
| 5 | 0 | 0 | 0 | 0 | 0 |
| 6 | 5 | 1 | 1 | 2 | 1 |
| 7 | 0 | 0 | 0 | 0 | 0 |

According to the results in table 7 above, only the detection of α-glucosidase activity using the 2-naphthyl-α-D-glucopyranoside substrate, strongly expressed by the *Staphylococcus aureus* strain, makes it possible to distinguish this species, which is coagulase positive, from the other staphylococcal species. For the other enzyme activities, the differences in intensity coloration between the *Staphylococcus aureus* strain and the strains of the other species are much less significant and make it difficult to distinguish between the various species. It should be noted that, in the case of a naphthol-based chromogenic substrate, the distinction of a coagulase-positive *Staphylococcus* such as *Staphylococcus intermedius* is not possible. The other Staphylococci, *Staphylococcus saprophyticus*, *Staphylococcus epidermidis* and *Staphylococcus haemolyticus*, are coagulase negative.

Experiment 5: Detection of α-glucosidase with Other Non-Chromogenic Substrates, such as a Fluorescent Substrate:

The media below were prepared in the base of the medium described in experiment 1, but in the absence of agar and in the presence of a fluorescent substrate instead of a chromogenic substrate. In order to underline the advantage of using a fluorescent substrate for demonstrating the coagulase-positive staphylococcal species, four fluorescent substrates, described in table 8, specific for the following enzyme activities, were compared:

TABLE 8

Abbreviations for the fluorescent substrates tested.

| FLUORESCENT SUBSTRATE | ABBREVIATION USED | ENZYME ACTIVITY |
|---|---|---|
| 4-methylumbelliferyl-α-D-glucoside | 4-MU-α-GLU | α-glucosidase |
| 4-methylumbelliferyl-β-D-glucoside | 4-MU-β-GLU | β-glucosidase |
| 4-methylumbelliferyl-β-D-galactoside | 4-MU-β-GAL | β-galactosidase |
| 4-methylumbelliferyl-β-D-glucuronide | 4-MU-β-GUR | β-glucuronidase |

The substrates are solubilized in the solvent used in experiments 1 and 2, the final concentration of each substrate is 200 mg/l of medium.

The various liquid media are distributed into the cupules of a support the size of a bank card, specific for the automated VITEK 2 (trademark) system of the company bioMérieux. The VITEK 2 system with integrated incubator handles all the steps, from the inoculation to the reporting of the results. Only the preparation of the inoculum at 0.5 McFarland is carried out by the operator, using a nephelometer, for each one of the strains tested directly in tubes specific to the system. The automated system makes it possible to read the bacterial growth by nephelometry, and the enzyme activity by fluorescence, at regular 15 minute intervals and over a period of 19 hours.

As in experiments 1, 2 and 4, the strains studied are part of the bioMérieux internal collection.

The results, given in table 9 below, represent the incubation time, in hours, required to obtain the maximum level of fluorescence which can be measured by the device:

TABLE 9

Table summarizing the results in hours of
incubation required to obtain the maximum
level of fluorescence of each enzyme activity
for each one of the strains.

| SPECIES | 4-MU-α-GLU | 4-MU-β-GLU | 4-MU-β-GUR | 4-MU-β-GAL |
|---|---|---|---|---|
| S. aureus 276 | 7 | 6 | 3 | 3 |
| S. aureus 070 | 8 | 4 | 3 | 3 |
| S. epidermidis 009 | 19 | 8 | 4 | 4 |
| S. xylosus 008 | 11 | 9 | 5 | 5 |
| S. saprophyticus 030 | 19 | 9 | 19 | 12 |
| S. haemolyticus 131 | 19 | 7 | 19 | 12 |
| S. intermedius 075 | 5 | 7 | 2 | 2 |

Analysis of the results shows that, by detecting α-glucosidase activity using an umbelliferone-based fluorescent substrate, it is possible to distinguish the coagulase-positive species (*Staphylococcus aureus* and *Staphylococcus intermedius*) from the coagulase-negative species (*Staphylococcus epidermidis*, *Staphylococcus xylosus*, *Staphylococcus saprophyticus* and *Staphylococcus haemolyticus*) as a function of the reading time. Specifically, hydrolysis of the 4-MU-α-GLU substrate by α-glucosidase makes it possible to obtain a maximum level of fluorescence before 8 hours of incubation for the coagulase-positive staphylococcal strains and after 10 hours of incubation for the coagulase-negative strains.

For the three other substrates studied, it appears to be difficult to distinguish the coagulase-positive staphylococcal species from the coagulase-negative staphylococci such as *Staphylococcus epidermidis*, since the amount of time to reach the maximum level of fluorescence for the species is very close, or even virtually identical, to that given by the coagulase-positive species.

This example clearly illustrates one of the advantages of detecting α-glucosidase activity using a fluorescent substrate.

Experiment 6: Mixture of Inhibitors which Promote the Detection of α-Glucosidase, with Enzyme Substrates According to the Invention:

Many studies were carried out in order to further enhance the specificity of our substrates. Among the solutions envisaged, the possibility of adding inhibitors resulted in a solution which was quite surprising and particularly advantageous.

Certain combinations of inhibitors were envisaged since no inhibitor could on its own enable the detection of staphylococci to be enhanced. Among these, most dissuade those skilled in the art from continuing to seek a solution along these lines, this being the case, for example, of:

The first combination is that of three inhibitors, lithium chloride LiCl (2 g/l), amphotercin (0.005 g/l) and aztreonam (0.008 g/l). Staphylococcal growth is very slightly affected by these three compounds; on the other hand, there is no effect on the enzyme activities detected (α-glucosidase and β-glucuronidase).

The second composition of the mixture of inhibitors is identical to the preceding test, only the concentrations of LiCl (ranging from 3 g/l to 7 g/l) and aztreonam (at the same time ranging from 0.008 g/l to 0.003 g/l) are modified simultaneously (preparation of a range of cross concentrations). As the concentration of LiCl increases, the Staphylococcal growth decreases. This effect is not observed for aztreonam, the increase in concentration does not disturb the bacterial growth. As regards the enzyme activities, there is no effect of the inhibitors (whatever the concentration) on the detection of α-glucosidase and of β-glucuronidase. The selectivity is enhanced as the concentration of inhibitors increases, but the Staphylococcal fertility is decreased.

The preceding mixture of inhibitors is completed, firstly, with colistin and, secondly, by an increase in the concentration of aztreonam. This increase, along with the addition of colistin to the medium, has virtually no effect on the staphylococcal growth. The selectivity is, moreover, enhanced since the critical species identified in the preceding tests are inhibited under these new conditions. The sensitivity of detection of α-glucosidase is very slightly decreased in the presence of aztreonam, whatever the concentration used (from 0. to 32 mg/l).

The performance levels of the medium, Staphylococcal and non- Staphylococcal fertility and expression of enzyme activities, are evaluated in the presence of the mixture of inhibitors defined in the preceding test (LiCl, aztreonam, amphotericin and colistin) but over a broader sample of strains. Addition of the four selective agents to the medium causes only a very slight decrease in the Staphylococcal growth and, overall, has no effect on the level of expression of α-glucosidase in *Staphylococcus aureus*. On the other hand, the detection/expression of β-glucuronidase activity is significantly altered in the presence of these inhibitors. The selectivity is still not perfect, in particular with respect to *Listeria, Enterococcus faecium, Klebsiella pneumoniae, Acinetobacter baumanii* and *Bacillus*.

Next, the vibriostatic compound O/129 was added, the concentration of aztreonam was increased (32 mg/11), the colistin was removed from the mixture of the inhibitors, and the β-glucosidase activity was characterized. The experiment below was carried out in the following medium:
20.1 g/l of peptone,
0.65 g/l of Tris buffer,
14 g/l of agar,
0.125 g/l of 6-chloro-3-indoxyl-β-D-glucoside,
0.100 g/l of 5-bromo4-chloro-3-indoxyl-N-methyl-α-D- glucoside,
0.0018 g/l of manganese chloride, and
4 g/l of sodium pyruvate.

Furthermore, the mixture of inhibitors has the following composition:
5 g/l of LiCl,
0.010 g/l of O/129,
0.032 g/l of aztreonam, and
0.005 g/l of amphotericin All the performance levels of the medium are surprising good. Specifically, the growth of the Staphylococcal species is correct. Moreover, detection of the α-glucosidase and β-glucosidase activities is not effected by the inhibitors and the level of selectivity is satisfactory since the growth of non-Staphylococci (*Listeria, Acinetobacter, Klebsiella*, etc.) is inhibited.

Experiment 7: Enhancement of Sensitivity for Weak Inocula by Adding Maltose:

The experiment below was carried out in media containing:
20.1 g/l of peptone,
0.65 g/l of Tris buffer,
14 g/l of agar,
0.125-0.125 g/l of 6-chloro-3-indoxyl-β-D-glucoside,
0.100 g/l de 5-bromo-4-chloro-3-indoxyl-N-methyl-α-D- glucoside,
0.004 g/l of manganese chloride,
4 g/l of sodium pyruvate,
4 g/l of lithium chloride,
0.032 g/l of aztreonam,
0.002 g/l of amphotericin, and
maltose at a final concentration of 0 or 0.1 or 0.3 or 0.4 g/l.

The maltose is solubilized in water at a concentration of, for example, 100 g/l, and then a sufficient volume to obtain the final concentrations above is added to the three molten media. The Staphylococcal strains derived from the bioMérieux internal collection were seeded onto each one of the chromogenic media on their own (closely spaced perpendicular streaks over the entire surface of the dish) using a suspension at 0.5 MacFarland diluted to 1/30000. The dishes were incubated at 37° C. for 48 hours. The colonies formed were examined visually after 18, 24 and 48 hours of incubation and the intensity of coloration of the colonies was marked.

Among the concentrations tested, the best results were obtained with 100 and 300 mg/l of maltose; these are concentrations which are therefore given in table 10 below. Even though the results with 400 mg/l of maltose are quite good, there may be false positive since some other coagulase-negative Staphylococci also possess α-glucosidase activity.

TABLE 10

Evaluation of the effect of maltose on the α-glucosidase activity of Staphylococci

| | | Intensity of coloration of the *S. aureus* colonies Maltose | | | |
|---|---|---|---|---|---|
| Strains | | 0 mg/l | 100 mg/l | 300 mg/l | 400 mg/l |
| 1 | 18 h | 0.8 | 1.3 | 1.3 | 1.7 |
| (*S. aureus* | 24 h | 1.3 | 1.7 | 1.7 | 3 |
| 7509008) | >40 h | 2 | 2 | 2 | 2.7 |
| 2 | 18 h | 2.3 | 2 | 2 | 2 |
| (*S. aureus* | 24 h | 3 | 2.7 | 2.7 | 2.7 |
| 8507276) | >40 h | 3 | 3 | 3 | 3 |
| 3 | 18 h | 0.3 | 1.3 | 1.3 | 1.3 |
| (*S. aureus* | 24 h | 1 | 1.7 | 1.7 | 2 |
| 8311065) | >40 h | 2.3 | 2.7 | 2.7 | 2.7 |
| 4 | 18 h | 0 | 0 | 0 | 0 |
| (*S. aureus* | 24 h | 0.1 | 0.3 | 0.3 | 0.3 |
| 8507285) | >40 h | 0.3 | 0.8 | 1 | 1.3 |
| 5 | 18 h | 0 | 0.3 | 0.5 | 0.5 |
| (*S. aureus* | 24 h | 0.1 | 0.5 | 1 | 1 |
| 0201035) | >40 h | 0.1 | 0.8 | 1 | 1.3 |
| 6 | 18 h | 0 | 0.3 | 0.3 | 0.3 |
| (*S. intermedius* | 24 h | 0.1 | 0.6 | 0.8 | 1 |
| 8407075) | >40 h | 0.6 | 0.8 | 1 | 1.3 |

The coloration was noted and the intensity of these colorations was marked. The reading scale is the same as that used above for tables 2 and 4.

Maltose therefore activates the α-glucosidase expression of *Staphylococcus aureus* and in particular of the critical strains (3, 4, 5 and 6), thus enabling these strains to generate green/light green colonies on the media containing maltose, whereas the colonies would have remained white in the absence of maltose, with a risk of giving a non-*staphylococcus aureus* identification as explained above.

Miscellaneous:

The following chromogenic substrates, which reveal α-glucosidase, can be obtained from the following companies:
 5-bromo-4-chloro-3-indoxyl-α-D-glucoside from BIOSYNTH in Staad, Switzerland under the reference B-7230,
 6-chloro-3-indoxyl-α-D-glucoside from BIOSYNTH mentioned above and bears the reference C-5015, and
 6-bromo-3-indoxyl-α-D-glucoside, the synthesis of which is described in patent no. WO 99/50438 of the company Inalco, and 2-naphthyl-α-D-glucopyranoside, which is well known to those skilled in the art and which can be obtained from the company Sigma for example.

The fluorescent substrate 4-methylumbelliferyl-α-D-glucoside, which reveals α-glucosidase, is well known to those skilled in the art and can be obtained from the company Sigma for example.

As regards 5-bromo-4-chloro-3-indoxyl-N-methyl-α-D-glucoside, it can be synthesized in the following way:
 5-bromo-4-chloro-1-methylindol-3-yl-α-D-glucoside, of the formula below:

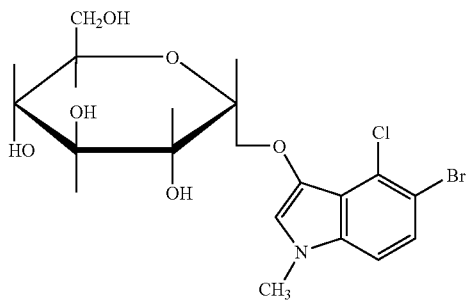

is obtained from 5-bromo-4-chloro-3-indolyl acetate or from 5-bromo-4-chloroindolyl 1,3-diacetate.

Step 1: Synthesis of 5-bromo-4-chloro-N-methyl-3-indolyl acetate 3 mmol of one or other ester above are dissolved in 35 ml of anhydrous diethyl ester and methylated on the nitrogen in the 1-position by adding an excess of diazomethane-boron trifluoride complex in ether. The organic phase is extracted with 1 M hydrochloric acid, washed with water and dried ($Na_2SO_4$). The solvent is removed and the residue is dried under vacuum in the presence of phosphorous pentoxide so as to obtain 0.62 g of product.

Step 2: Synthesis of 5-Bromo-4-chloro-1-methyl-3-indolyl-α-D-glucoside

A. The N-methylated acetate ester obtained above (0.6 g, 2 mmol) is dissolved in anhydrous ethyl acetate and hydrolyzed by adding an excess of methanolic aqueous ammonia under an argon atmosphere. After 16 hours at ambient temperature, the solvent and the excess ammonia are removed by evaporation under reduced pressure, and the solid residue is directly glycosilated without further purification.

B. The 5-bromo-4-chloro-1-methylindol-3-yl is taken up in dichloromethane and treated at 0° C. with a solution of glucose pentaacetate in dichloromethane (1.45 g, 5 mmol/20 ml) and then with tin chloride (2 mmol) dissolved in dichloromethane, with stirring. The reaction is continued overnight and the product is isolated by stirring with 1 M glacial hydrochloric acid. After removal of the tin salts, the organic phase is filtered through PHASE-SEP paper and dried over $MgSO_4$. In TLC, two spots are detected under UV. After a first separation on a silica gel column, with dichloromethane-ethyl acetate as eluant, the two compounds are separately deacetylated in the presence of a methanolic solution of sodium methoxide, to give mixtures of α- and β-glucoside.

C. The α form appears to be predominant, the residual β-glucoside can be removed by dissolving in water which is hot, cooled to 37° C. and incubated in the presence of β-glucosidase. The solution is filtered and the indigo pigments are extracted with ether. The residual aqueous solution is evaporated under reduced pressure and then lyophilized so as to obtain the α-glucoside (120 mg).

The chromogenic substrate 6-chloro-3-indoxyl-β-D-glucuronide, which reveals β-glucuronidase, can be obtained from BIOSYNTH, still in Staad, Switzerland, under the reference C-5050.

The chromogenic substrate 5-bromo-4-chloro-3-indoxylβ-D-glucuronide, which also reveals β-glucuronidase, can be obtained from BIOSYNTH under the reference B-7400.

The chromogenic substrate 6-chloro-3-indoxyl-β-D-galactoside, which reveals β-galactosidase, can be obtained from BIOSYNTH under the reference C-5000.

The chromogenic substrate 5-bromo-4-chloro-3-indoxylβ-D-glucoside, which reveals β-glucosidase, can be obtained from BIOSYNTH under the reference B-7250.

The invention claimed is:

1. A medium for the detection of *Staphylococcus aureus* and/or of coagulase-positive Staphylococci, which comprises a *Staphylococcus aureus* culture medium and at least one enzyme substrate for demonstrating α-glucosidase activity, wherein the enzyme substrate for demonstrating α-glucosidase activity is a chromogenic or fluorescent agent and is indoxyl-based, umbelliferone-based, or napthol-based, said medium further comprising at least one inhibitor which favors the growth of *Staphylococcus aureus* and/or of coagulase-positive Staphylococci.

2. The medium according to claim 1, wherein the chromogenic agent is selected from the group consisting of:
 6-bromo-3-indoxyl-α-D-glucoside,
 5-bromo-4-chloro-3-indoxyl-α-D-glucoside,
 5-bromo-4-chloro-3-indoxyl-N-methyl-α-D-glucoside,
 6-chloro-3-indoxyl-α-D-glucoside,
 4-methylumbelliferyl-α-D-glucoside, and combinations thereof.

3. The medium according to claim 1, for the detection of *Staphylococcus aureus*, wherein the chromogenic agent for demonstrating α-glucosidase activity is naphthol-based.

4. The medium according to claim 1 wherein the chromogenic agent is 2-naphthyl-α-D-glucopyranoside.

5. The medium according to claim 1 which further comprises at least one enzyme substrate for detecting osidase, esterase, peptidase, or coagulase activity.

6. The medium according to. Claim 5, which comprises two chromogenic agents chosen from the following pairs:
- 5-bromo-4-chloro-3-indoxyl-N-methyl-α-D-glucoside combined with 5-bromo-6-chloro-3-indoxyl-β-D-galactoside,
- 5-bromo-4-chloro-3-indoxyl-N-methyl-α-D-glucoside combined with 6-chloro-3-indoxyl-β-D-glucuronide,
- 6-chloro-3-indoxyl-α-D-glucoside combined with 5-bromo-4-chloro-3-indoxyβ-D-glucuronide, or
- 6-chloro-3-indoxyl-α-D-glucoside combined with 5-bromo-4-chloro-3-indoxyβ-D-glucoside.

7. The medium according to claim 1, wherein the at least one inhibitor is a mixture of the following inhibitors:
- lithium chloride,
- 2,4-diamino-6,7-diisopropylpteridine,
- aztreonam, and
- amphotericin.

8. The medium according to claim 1, further comprising maltose.

9. A method for identifying *Staphylococcus aureus* in a sample containing at least one species of bacterium, which method comprises the following steps:
- inoculating a medium according to claim 1 with a portion of the sample, and
- incubating the inoculated medium so as to produce bacterial colonies of sufficient size to observe the coloration of each chromogenic agent or the fluorescence of each fluorescent agent, which has reacted in said medium.

10. The method according to claim 9, further comprising counting the colonies identified by coloration or a fluorescence related to *Staphylococcus aureus*.

11. A medium according to claim 5 wherein said other enzyme substrate is for detecting the activity of at least one osidase selected from the group consisting of β-glucosidase, β-glucuronidase and β-galactosidase.

12. A medium according to claim 1, wherein the at least one inhibitor is selected from the group consisting of lithium chloride, sodium azide, colistin, amphotericin, aztreonam, colimicin, sodium chloride and Deferoxamine.

13. A medium for the detection of *Staphylococcus aureus* and/or of coagulase-positive Staphylococci, which comprises a *Staphylococcus aureus* culture medium, maltose, and at least one enzyme substrate for demonstrating α-glucosidase activity, wherein the enzyme substrate for demonstrating α-glucosidase activity is a chromogenic or fluorescent agent, and wherein the maltose is present at a concentration of between 100 and 300 mg/l.

14. The medium according to claim 1, wherein the chromogenic or fluorescent agent is indoxyl-based or umbelliferone-based.

* * * * *

UNITED STATES PATENT AND TRADEMARK OFFICE
CERTIFICATE OF CORRECTION

PATENT NO. : 7,807,439 B2  
APPLICATION NO. : 10/473835  
DATED : October 5, 2010  
INVENTOR(S) : Christine Cotte et al.

Page 1 of 1

It is certified that error appears in the above-identified patent and that said Letters Patent is hereby corrected as shown below:

The title page, item (73), "Mary" should read --Marcy--.

Column 19:

line 1, "to. Claim" should read --to claim--;

line 10, "5-bromo-4-chloro-3 indoxyβ-D-glucuronide" should read --5-bromo-4-chloro-3 indoxyl-β-D-glucuronide--;

line 12, "5-bromo-4-chloro-3 indoxyβ-D-glucoside" should read --5-bromo-4-chloro-3-indoxyl-β-D-glucoside--.

Signed and Sealed this  
Nineteenth Day of July, 2011

David J. Kappos  
*Director of the United States Patent and Trademark Office*